(12) United States Patent
Park et al.

(10) Patent No.: US 11,400,012 B2
(45) Date of Patent: Aug. 2, 2022

(54) VISION RECOVERY TRAINING DEVICE

(71) Applicant: Sung Yong Park, Busan (KR)

(72) Inventors: Sung Yong Park, Busan (KR); Kyung Hyun Noh, Busan (KR)

(73) Assignee: Sung Yong Park

( * ) Notice: Subject to any disclaimer, the term of this patent is extended or adjusted under 35 U.S.C. 154(b) by 768 days.

(21) Appl. No.: 16/395,624

(22) Filed: Apr. 26, 2019

(65) Prior Publication Data

US 2019/0247267 A1 Aug. 15, 2019

Related U.S. Application Data

(63) Continuation of application No. PCT/KR2017/012605, filed on Nov. 8, 2017.

(30) Foreign Application Priority Data

Nov. 8, 2016 (KR) ........................ 10-2016-0148210
Jun. 30, 2017 (KR) ........................ 10-2017-0083784

(51) Int. Cl.
*A61B 3/00* (2006.01)
*A61H 5/00* (2006.01)
(Continued)

(52) U.S. Cl.
CPC ............... *A61H 5/00* (2013.01); *A61F 9/02* (2013.01); *G02B 7/00* (2013.01); *G02B 7/021* (2013.01);
(Continued)

(58) Field of Classification Search
CPC .............. A61H 5/00; A61H 2201/0157; A61H 2201/0192; A61H 2201/1215; A61H 2201/1604; A61H 2201/1607; A61H 2201/165; A61H 2201/5064; A61H 2205/024; G02B 7/00; G02B 7/021; G02B 7/023; G02B 7/14; G02B 7/16; G02B 26/00; A61F 9/02
(Continued)

(56) References Cited

U.S. PATENT DOCUMENTS

| 4,698,564 A | 10/1987 | Slavin |
| 5,648,833 A | 7/1997 | Doms et al. |
| 2015/0137646 A1 | 5/2015 | Tsuchida et al. |

FOREIGN PATENT DOCUMENTS

| CN | 1536141 A | 10/2004 |
| CN | 203193417 U | 9/2013 |

(Continued)

OTHER PUBLICATIONS

European Search Report (EP 17868848.7), EPO, dated Oct. 10, 2019.
(Continued)

*Primary Examiner* — William Choi
(74) *Attorney, Agent, or Firm* — Park & Associates IP Law, P.C.

(57) ABSTRACT

An embodiment of the disclosure provides a vision recovery training device, which includes a housing formed to be worn on a face around the eyes, a pair of rotation modules mounted to an inside of the housing, and a lens provided in each rotation module, at least one of the rotation modules including: a rotation disc; a magnetic body inserted in the rotation disc; and a sensor module provided in the housing at a radial position corresponding to the magnetic body.

9 Claims, 6 Drawing Sheets

(51) Int. Cl.
   *A61F 9/02*    (2006.01)
   *G02B 26/00*   (2006.01)
   *G02B 7/14*    (2021.01)
   *G02B 7/02*    (2021.01)
   *G02B 7/00*    (2021.01)
   *G02B 7/16*    (2021.01)

(52) U.S. Cl.
   CPC ............. *G02B 7/023* (2013.01); *G02B 7/14* (2013.01); *G02B 7/16* (2013.01); *G02B 26/00* (2013.01); *A61H 2201/0157* (2013.01); *A61H 2201/0192* (2013.01); *A61H 2201/1215* (2013.01); *A61H 2201/1604* (2013.01); *A61H 2201/165* (2013.01); *A61H 2201/1607* (2013.01); *A61H 2201/5064* (2013.01); *A61H 2205/024* (2013.01)

(58) Field of Classification Search
   USPC .......................................................... 351/203
   See application file for complete search history.

(56) References Cited

FOREIGN PATENT DOCUMENTS

| | | |
|---|---|---|
| EP | 1980197 A1 | 10/2008 |
| JP | S63-79633 A | 4/1988 |
| JP | H8182649 A | 7/1996 |
| JP | 2001-037125 A | 2/2001 |
| JP | 2008-005879 A | 1/2008 |
| JP | 2010-088539 A | 4/2010 |
| KR | 20-1995-0008988 U | 4/1995 |
| KR | 10-2002-0019776 A | 3/2002 |
| KR | 20-0350714 Y1 | 5/2004 |
| KR | 20-2012-0003877 U | 6/2012 |
| KR | 10-2016-0097858 A | 8/2016 |
| KR | 10-2016-0097864 A | 8/2016 |

OTHER PUBLICATIONS

International Search Report (PCT/KR2017/012605), WIPO, dated Mar. 5, 2018.

VISION RECOVERY TRAINING DEVICE

REFERENCE TO RELATED APPLICATIONS

This is a continuation of International Patent Application PCT/KR2017/012605 filed on Nov. 8, 2017, which designates the United States and claims priority of Korean Patent Application No. 10-2016-0148210 filed on Nov. 8, 2016, and Korean Patent Application No. 10-2017-0083784 filed on Jun. 30, 2017, the entire contents of which are incorporated herein by reference.

FIELD OF THE INVENTION

The disclosure relates to a vision recovery training device for preventing an error in settings of an initial position when a diopter is changed.

BACKGROUND OF THE INVENTION

A structure that a human eye has is a kind of convex lens, in which external light enters a magnifying lens, i.e. a cornea and a crystalline lens of the eye, is focused as an inverted image on a retina at a focal distance by refraction in the magnifying lens, is reflected from the retina serving as a mirror, and passes through the magnifying lens, i.e. the crystalline lens and the cornea while changing the inverted image into an magnified erect image, thereby making a brain recognize the same magnified erect thing as that of the outside world visible to the eyes.

In this case, by contraction and relaxation of a ciliary body connected to the crystalline lens, the crystalline lens becomes thicker when looking closely and has normal thickness when looking far away. If someone reads a book or watches TV at a close distance over a long period of time or frequently and repeatedly, his/her crystalline lens being thick is difficult to return to its original state and thus s/he may become near-sighted. Such a myopic patient wears glasses with concave lenses to compensate for the increased thickness of the crystalline lens and correct his/her eyesight. However, the glasses make the myopic patient see things well, but lower his/her restorative abilities to thereby cause a problem that the crystalline lens being thick becomes hardened.

Meanwhile, a vision-information processing function refers to a process for information between eyes and a brain, which is also called a vision function. In other words, the vision-information processing function refers to that information input based on senses of touch, smell and hearing and information input based on sensed of sight are quickly sent to a brain and the brain synthetically interprets such information. With this vision-information processing function, it is possible to perceive a sense of distance, a sense of speed, a sense of three dimension, etc.

The vision-information processing function is almost irrelevant to whether eyesight is good or poor. When there is a problem with the vision-information processing function, it may be difficult to have sports or leports activities, read a book, maintain attention and concentration, or write an article. Therefore, such problems may be followed by reading disabilities, dyslexia, attention deficit disorder, learning disabilities, writing disabilities, social disabilities, or etc.

The problem with the vision-information processing function may arise when visual perception is excessively used (for doing homework, reading a book, using a computer, watching TV, etc.) while eyeballs are growing. Such problems with the vision-information processing function may include binocular dysfunction, control disorder, etc.

The binocular dysfunction may be caused when extraocular muscles supporting a pupil do not normally function, and the control disorder may be caused when the contraction and relaxation for the crystalline lens are abnormally made.

Accordingly, there have been proposed vision recovery training device as a vision improving device, in which the muscles are exercised and strengthened by changing a diopter of a lens arranged in front of eyeballs.

However, a conventional vision recovery training device has a problem of malfunctioning due to an error in settings of an initial position value for a diopter lens while rotation is made using various driving motors to change the diopter.

SUMMARY OF THE INVENTION

The disclosure is conceived to solve the foregoing conventional problems, and the object of the disclosure is to provide a vision recovery training device, which can readily enhance each individual vision of wearers without separately preparing glasses adjusted for their vision.

According to an aspect of the disclosure, there is provided a vision recovery training device, which includes a housing formed to be worn on a face around the eyes, a pair of rotation modules mounted to an inside of the housing, and a lens provided in each rotation module, at least one of the rotation modules including: a rotation disc; a magnetic body inserted in the rotation disc; and a sensor module provided in the housing at a radial position corresponding to the magnetic body.

According to an embodiment, the rotation disc may be formed with an insertion hole, and the magnetic body may be coupled to the insertion hole.

According to an embodiment, the device may further include a plurality of projections protruding from an inner circumferential surface of the insertion hole along a lengthwise direction toward a center of the insertion hole radially.

According to an embodiment, the rotation disc may be rotatably supported on a rotary shaft formed in a support frame, and a plurality of lenses different in a refractive index may be radially arranged with respect to the rotary shaft and spaced apart at a predetermined distance.

According to an embodiment, the rotation disc may be formed with an insertion hole corresponding to at least one lens among the plurality of lenses, and the magnetic body is coupled to the insertion hole.

According to an embodiment, more than at least one of magnetic bodies provided in the insertion hole of the rotation disc may be different in magnetism, and the sensor module may be configured to identify a position corresponding to each lens.

According to an embodiment, the magnetic body may be shaped like a column having a predetermined length, in which N and S poles are at least one or more times alternately arranged along a circumference of a hollow of the column, and coaxially coupled to the inner circumference of the rotary shaft.

According to an embodiment, the sensor module may include a Hall sensor, and the Hall sensor may be arranged to be spaced apart from the magnetic body in a radial direction or an axial direction.

According to an embodiment of the disclosure, it is possible to prevent an error in settings of an initial position when a diopter is changed.

Further, there is an effect on readily enhancing each individual vision of wearers without additional glasses adjusted for their vision.

It will be understood that the effects of the disclosure are not limited to the foregoing effects, but include all effects deducible from the features disclosed in the detailed description or appended claims.

DETAILED DESCRIPTION OF THE INVENTION

Figure 1:
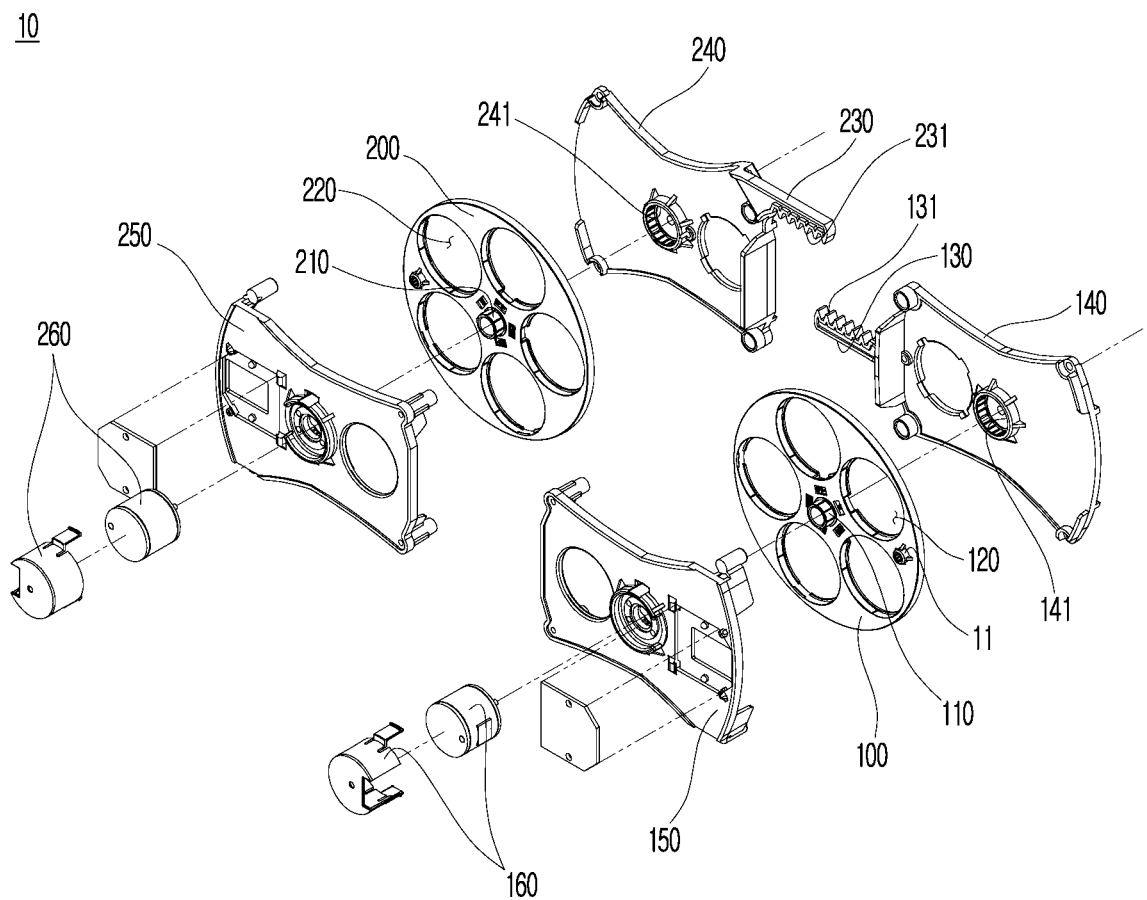
FIG. 1 is an exploded perspective view of a vision recovery training device according to an embodiment of the disclosure.

Hereinafter, the disclosure will be described with reference to accompanying drawings. However, the disclosure may be embodied in various forms, and is thus not limited to the embodiments set forth herein. In the drawings, parts unrelated to the descriptions will be omitted for clearly describing the disclosure, and like numerals refer to like elements throughout.

Throughout the disclosure, "connection" between a part and another part includes not only "direct connection" but also "indirect connection" leaving intermediate member in between. Further, when a part "includes" an element, it means that the part may not exclude another element but include another element unless otherwise noted.

Below, embodiments of the disclosure will be described in detail with reference to the accompanying drawings.

Figure 2:
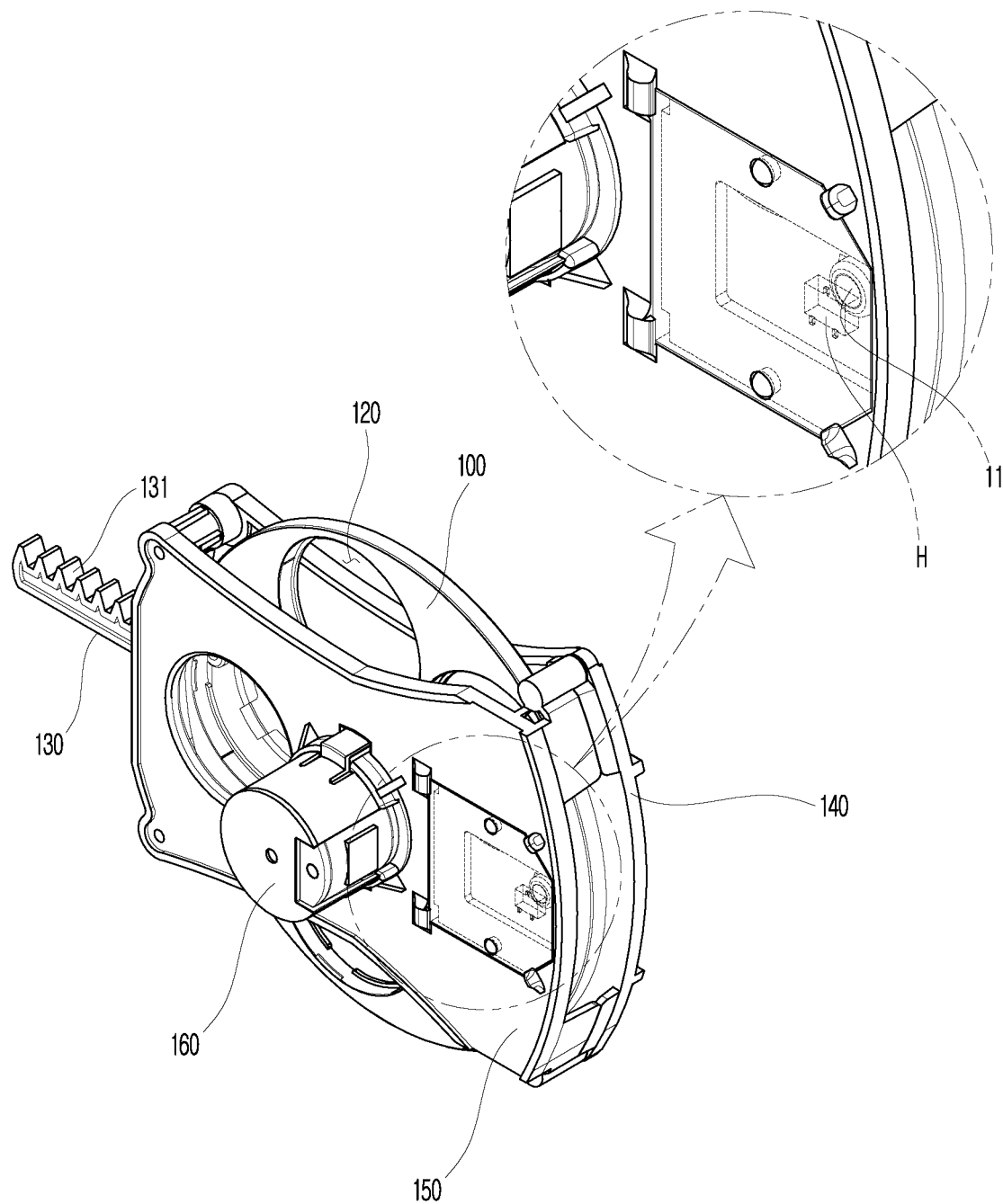
FIG. 2 is an enlarged view of a sensor module and a magnetic body in FIG. 1.
Figure 3:
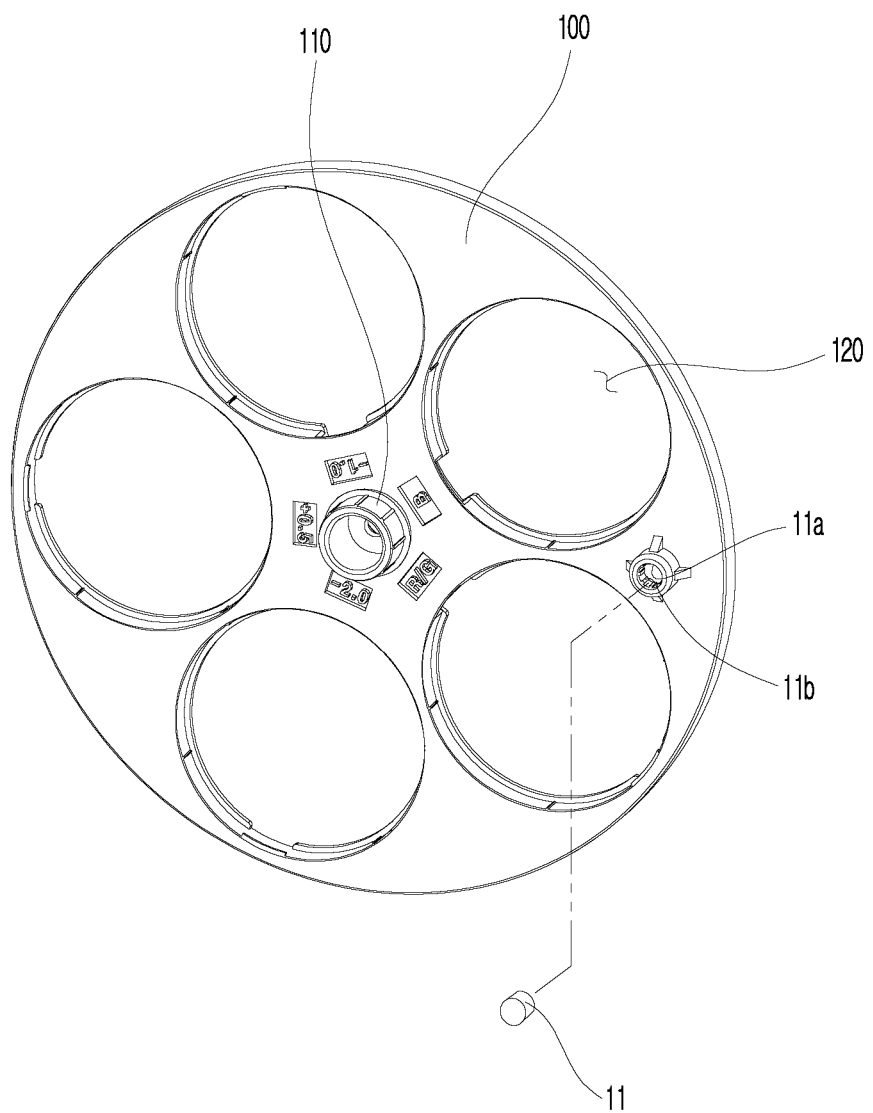
FIG. 3 is a perspective view of illustrating a separated state of a rotation disc in FIG. 1.

FIG. 1 is an exploded perspective view of a vision recovery training device according to an embodiment of the disclosure, FIG. 2 is an enlarged view of a sensor module and a magnetic body in FIG. 1, and FIG. 3 is a perspective view of illustrating a separated state of a rotation disc in FIG. 1.

As shown in FIG. 1 to FIG. 3, a vision recovery training device according to an embodiment of the disclosure may include a housing (not shown) formed to be worn on a face around eyes, and a pair of rotation modules 10 rotating as mounted to the inside of the housing.

Here, the housing includes one side formed with a fitting surface (not shown) corresponding to and completely fitted on a contour around a user's eyes, and the other side having an accommodating space to be mounted with a rotation module 10.

Further, an inner side corresponding to a user's face is curved with a pair of opening holes (not shown) in regions respectively corresponding to a pair of eyes and opened having a predetermined size. The pair of opening holes is formed to arrange a center point of each circle on an axial line.

The rotation module 10 may include one pair of rotation discs 100 and 200, a magnetic body 11, and a sensor module H. Here, the sensor module H in this embodiment employs a Hall sensor H, but various other sensors may be used as long as they can measure magnetism of a magnetic body 11.

The rotation discs 100 and 200 may be interposed between a pair of rear support frames 140 and 240 arranged at a rear side, and a pair of front support frames 150 and 250 arranged at a front side.

Although this embodiment illustrates that one pair of rotation discs 100 and 200 is interposed between one pair of support frames 150 and 250 and the other pair of support frames 140 and 240, a single support frame may be provided and a single rotation disc may be rotatably coupled to the single support frame.

However, when one pair of rotation discs 100 and 200 is provided, the rotation discs 100 and 200 have the same symmetrical shapes with each other. Therefore, for convenience of description, one rotation disc 100 and the support frames 140 and 150 will be representatively described The rotation disc 100 has a flat circular shape and forms one of the pair having a parallel rotary shaft 110. Here, the rotary shaft 110 may be hinge-coupled to the support frames 140 and 150.

Further, according to this embodiment, the support frames 140, 150, 240 and 250 are separated front and rear frames and the rotary shaft 110 is interposed between the front and rear frames. Alternatively, only one support frame may be provided, and the rotary shaft may be coupled to such one support frame. In this case, it is natural that one rotary shaft is used.

On the rotation disc 100, a plurality of different diopter lenses (not shown) may be radially arranged at regular intervals with respect to the rotary shaft 110. For convenience of description, FIGS. 1 and 2 illustrate only holes 120 without the diopter lenses. However, the diopter lens having a matching diameter may be mounted to each of the holes 120

The rotation disc 100 may rotate so that the plurality of diopter lenses different in prescription can rotate step by step like a revolver.

For example, when there are five diopter lenses, the rotation may be made by all five steps.

In this case, a step motor may be used. In other words, a position at which the sensor module H detects the magnetic body 11 may be set as an initial position of the rotation disc 100, which will be described later, and the rotation may be made as much as a preset angle per one pulse by the step motor during the rotation of the rotation disc 100, thereby maintaining an equiangular rotation of the rotation disc 100 through only one magnetic body 11.

One step described in the disclosure may refer a step of shifting to an adjacent diopter lens. Because the rotation is made step by step like a revolver to shift to the adjacent diopter lens, the diopter lens according to the disclosure may be called a revolver lens.

However, the number of diopter lenses may vary depending on use environments without limitations.

One pair of rotation discs 100 and 200 may move close to or away from each other by connection frames 130 and 230.

The connection frames 130 and 230 are to change a distance between the rotation discs 100 and 200 forming one pair.

Specifically, the connection frames 130 and 230 are respectively formed at intersecting positions on the opposite surfaces of support frames 140 and 240 forming one pair.

In other words, the connection frames 130 and 230 may include a first rack gear 131 and a second rack gear 231 arranged to respectively protrude upward and downward, a pinion gear (not shown) arranged to rotate as engaged between the first rack gear 131 and the second rack gear 231 and rotating to move the first rack gear 131 and the second rack gear 231 in the opposite directions to each other, and a connection gear (not shown) fastened to rotate integrally with the pinion gear and connected to a driving shaft of a driving module (not shown).

For example, as shown in FIGS. 1 and 2, one connection frame 130 horizontally protrudes from a lower end of one rear support frame 140 of one pair of support frames 140 and 240, and the other connection frame 230 may horizontally protrude from an upper end of the other rear support frame 240.

Although it is not shown, the first rack gear 131 and the second rack gear 231 are moved close to or away from each other by the rotation of the pinion gear engaging with the first rack gear 131 and the second rack gear 231, and thus adjusted to correspond to a space between eyes of a user.

The support frames 140, 150, 240 and 250 are coupled to each other to support the rotation of the rotation disc 100.

In a case of two rotation discs 100 and 200, the support frames 140 and 240 are formed with hinge holes 141 and 241 on one sides thereof to support the rotation of the rotation discs 100 and 200, and coupled to the other support frames 150 and 250 as rotary shafts 110 and 210 of the rotation discs 100 and 200 are coupled to the hinge holes 141 and 241, respectively.

Driving members 160 and 260 may be provided in the fronts of the support frames 150 and 250 and coaxially couple with the rotary shafts 110 and 210.

The driving members 160 and 260 may provide rotational force for driving the rotation discs 100 and 200 to rotate in one direction or the other direction. Here, the driving members 160 and 260 may include a step motor or the like to thereby achieve forward and backward rotations.

Referring back to FIGS. 1 and 2, one rotation disc 100 will be representatively described for convenience. The rotation disc 100 may include the magnetic body 11 inserted in the thickness direction thereof. In this case, the magnetic body 11 may be provided at a position near to one among the plurality of diopter lenses. Like this, the position of the magnetic body 11 is to set one among the plurality of diopter lenses as a reference point, details of which will be described later.

Specifically, the rotation disc 100 may be formed with an insertion hole 11a corresponding to at least one among the plurality of lenses, and the magnetic body 11 may couple with the insertion hole 11a. The magnetic body 11 maybe forcibly fitted to the insertion hole 11a. In this case, a plurality of projections 11b protruding along the lengthwise direction of the insertion hole 11a may be formed on an inner circumferential surface of the insertion hole 11a radially toward the center of the insertion hole 11a. Thus, the magnetic body 11 can be firmly coupled to the inner circumferential surface of the insertion hole 11a.

The magnetic body 11 may include a permanent magnet or the like shaped like a column having a predetermined height. As described above, the magnetic body 11 may be fitted so that its outer circumferential surface can meet the inner circumferential surface of the insertion hole 11a. Besides, the magnetic body 11 may include a material having various shapes and exerting a certain magnetic force as long as it can be in surface-contact with and be forcibly fitted to the insertion hole 11a.

The sensor module H may be fastened on to the inner surface of the housing.

The sensor module H may be installed on the inner surface of the housing at a position to face with the magnetic body 11 while the rotation disc 100 rotates.

In other words, the magnetic body 11 and the sensor module H are installed at respective positions to face with each other while both the rotation disc 100 and the magnetic body 11 are rotated together, and change in a direction of a magnetic field is detected as the magnetic body 11 repetitively moves close to or away from the sensor module H, thereby measuring change in Hall voltage.

An electric signal changed in this process is converted into an analog signal or a digital signal, and the position of the magnetic body 11 moving around the sensor module H is measured based on a conversion cycle of this signal.

As described above, it is possible to obtain information about the reference position of the rotation disc 100 as the sensor module H moves close to the magnetic body 11 when the rotation disc 100 rotates.

In other words, a moment when the magnetic body 11 of the rotation disc 100 comes close to the sensor module H is set as information about an initial position, and therefore the position where the magnetic body 11 is detected is identified as the initial position even through the rotation disc 100 is repetitively rotated forward and backward.

With this, in a case of using the vision recovery training device, a user controls the rotation disc 100 to rotate forward or backward so as to place a diopter lens of desired power to a position corresponding to the eyes, thereby maintaining the settings of the initial position of the rotation disc 100 while selecting the diopter lens for correction of eyesight.

In addition, it is possible to prevent malfunction due to loss of information about the previously set position of the rotation disc even though electric power supplied to the vision recovery training device is suddenly cut off.

Figure 4:
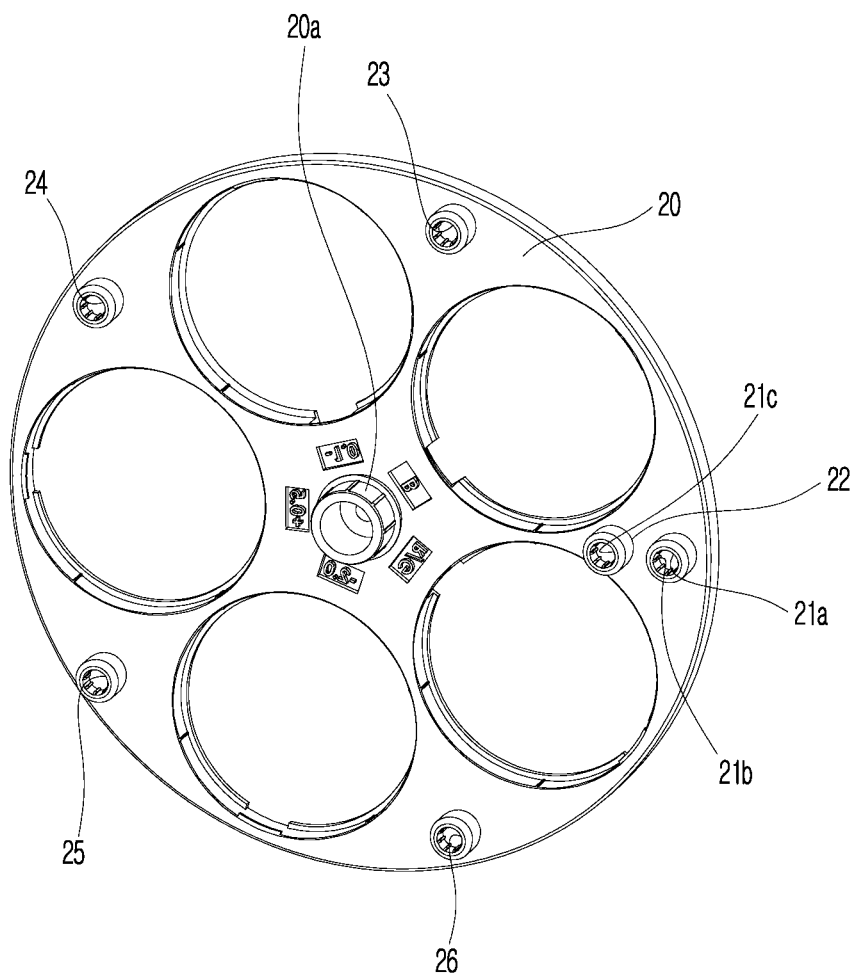
FIG. 4 is a perspective view of a vision recovery training device according to another embodiment of the disclosure.

FIG. 4 is a perspective view of a vision recovery training device according to another embodiment of the disclosure.

As shown in FIG. 4, a plurality of insertion holes 22, 23, 24, 25 and 26 may be provided on a rotation disc 20 in a thickness direction.

In this case, each of the insertion holes 21a, 22, 23, 24, 25 and 26 is fitted with a magnetic body on each inner circumference surface thereof, but they will be illustrated without the magnetic body for convenience of description.

The insertion hole 21a formed adjacent to the insertion hole 22 may be provided in such a manner that two insertion holes 21a and 22 are next to each other to be set as the initial position of the rotation disc 20. When two insertion holes 21a and 22 are provided adjoining one diopter lens among the plurality of diopter lenses, a position where magnetic flux density caused by two magnetic bodies is detected by a sensor module is set as the initial position.

The plurality of insertion holes 22, 23, 24, 25 and 26 may be radially arranged outward with respect to a rotary shaft 20a of the rotation disc 20.

In this case, a direct current (DC) motor may be employed so that a space between the other insertion holes 23, 24, 25 and 26 can be detected as much as an interval for the diopter lenses when the rotation disc 20 rotates.

When there are the plurality of insertion holes 22, 23, 24, 25 and 26, the magnetic bodies installed in the respective insertion holes 22, 23, 24, 25 and 26 may be different in magnetism and thus varied in magnetic flux density depending on the adjacent diopter lenses. Therefore, the diopter lens may be identified based on the corresponding magnetic body regardless of the initial position or rotated position of the rotation disc 20.

Figure 5:
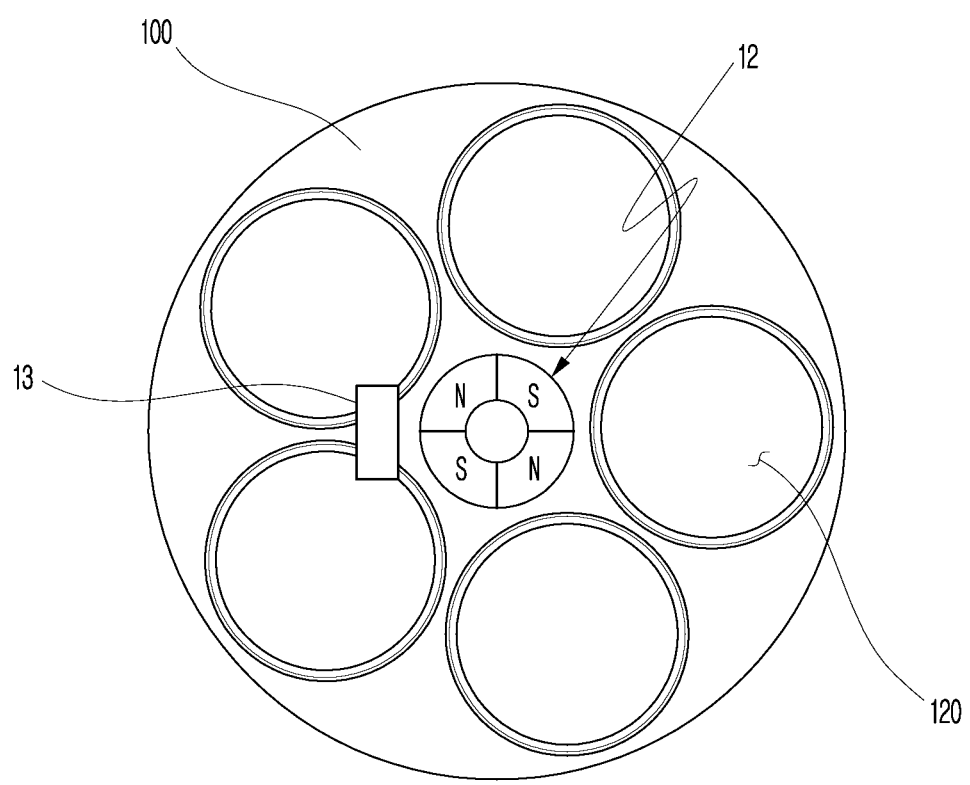
FIG. 5 is a plan view of a vision recovery training device according to still another embodiment of the disclosure.
Figure 6:
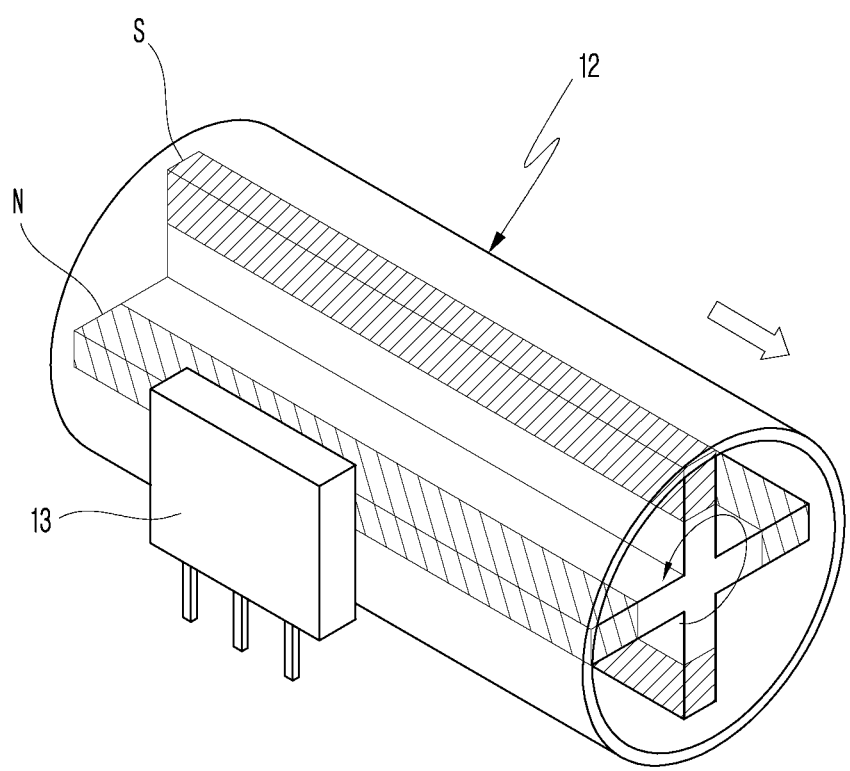
FIG. 6 illustrates an inside of a magnetic body in FIG. 5.

FIG. 5 is a plan view of a vision recovery training device according to still another embodiment of the disclosure, and FIG. 6 illustrates an inside of a magnetic body in FIG. 5.

As shown in FIGS. 5 and 6, a magnetic body 12 in a vision recovery training device according to this embodiment of the disclosure is shaped like a column having a predetermined length, in which N and S poles are alternately arranged along a circumference of a hollow of the column, and coaxially coupled to the inner circumference of the rotary shaft 110 of the rotation disc 100. Alternatively, the magnetic body 12 may have various shapes such as a cylinder, a polygonal prism, etc. having a predetermined length.

The features of FIGS. 5 and 6 are the same as those of FIGS. 1 and 2 except that the hollow magnetic body 12 having a predetermined length is coaxially arranged on the rotary shaft 110, and thus repetitive descriptions thereof will be avoided.

As shown in FIGS. 5 and 6, when the magnetic body 12 has a cylindrical shape, a projection is separately formed on an inner wall of a housing, and a sensor module 13 is mounted to the projection. Thus, the sensor module 13 may be installed at a position being spaced apart outward in a radial direction from the outer circumference of the cylindrical magnet 12.

Like those of FIGS. 1 and 2, the magnetic body 12 and the sensor module 13 are installed to face each other while both the rotation disc 100 and the magnetic body 12 are rotated at a time, and the S or N pole of the magnetic body 12 is alternately arranged at least one or more times around the sensor module 13 and repetitively close to or away from the sensor module 13 so that change in Hall voltage can be measured by detecting direction change in a magnetic field.

An electric signal changed in this process is converted into an analog signal or a digital signal, and the position of the pole of the magnetic body 12 moving around the sensor module 13 is measured based on a conversion cycle of this signal.

As described above, it is possible to obtain information about the reference position of the rotation disc 100 as the sensor module 13 moves close to the magnetic body 12 when the rotation disc 100 rotates.

In other words, a moment when the magnetic body 12 of the rotation disc 100 repetitively comes close to the sensor module 13 is set as information about the initial position, and therefore the position where a certain pole of the magnetic body 11 is detected is identified as the initial position even through the rotation disc 100 is repetitively rotated forward and backward.

Meanwhile, FIG. 6 illustrates that the sensor module 13 is arranged to be spaced apart from the outer circumference of the magnetic body 12, but the sensor module 13 may be arranged to be spaced apart from one direction along the axial direction of the magnetic body 12 and detect change in the magnetic fields of the alternately arranged different poles of the magnetic body 12.

Further, a plurality of polar members N and S of the magnetic body 12 may be different in magnetism. In this case, one polar member adjacent to the sensor module 13 is different in magnetic flux density from the other polar member, and therefore the diopter lens is identified based on the corresponding polar member regardless of the initial position or rotated position of the rotation disc 20.

The foregoing description of the disclosure is for illustrative purposes only, and it will be thus understood that various changes can be easily made without departing from technical concept of the disclosure or changing essential features by a person having an ordinary skill in the art to which the disclosure pertains. Therefore, the foregoing embodiments have to be understood not restrictively but illustratively in all aspects. For example, an element described as a singular form may be embodied as divided, and elements described as a divisional form may be embodied as combined.

The scope of the disclosure is defined by the appended claims, and it is appreciated that all changes or modifications made from the scope of the claims and their equivalents are included in the scope of the disclosure.

What is claimed is:

1. A vision recovery training device in eyes, comprising:
   a housing formed to be worn on a face around the eyes;
   a pair of rotation modules mounted to the housing, and each comprising a rotation disc and a magnetic body provided in the rotation disc; and
   a sensor configured to sense change in polarity of the magnetic body.

2. The vision recovery training device according to claim 1, wherein the rotation disc comprises an insertion hole in which the magnetic body is inserted.

3. The vision recovery training device according to claim 2, wherein the insertion hole comprises at least one projection on an inner circumferential surface thereof.

4. The vision recovery training device according to claim 1, further comprising a support frame configured to rotatably support the rotation disc,
   wherein the rotation disc comprises a plurality of lenses arranged at predetermined intervals radially with respect to a rotary shaft.

5. The vision recovery training device according to claim 4, wherein the rotation disc comprises an insertion hole provided corresponding to at least one lens among the plurality of lenses and mounted with the magnetic body.

6. The vision recovery training device according to claim 4, wherein
   a plurality of magnetic bodies are arranged corresponding to the plurality of lenses,
   the plurality of magnetic bodies are different in magnetism from each other, and
   the sensor is configured to identify a position corresponding to each lens by sensing different magnetism.

7. The vision recovery training device according to claim 1, wherein the magnetic body is shaped like a column having a predetermined length, in which N and S poles are at least one or more times alternately arranged along a circumference.

8. The vision recovery training device according to claim 7, wherein
   the sensor comprises a Hall sensor, and
   the Hall sensor is arranged to be spaced apart from the magnetic body in a radial direction or an axial direction.

9. The vision recovery training device according to claim 7, further comprising a support frame configured to rotatably support the rotation disc, wherein the magnetic body is arranged coaxially with the rotary shaft of the rotation disc.

* * * * *